United States Patent [19]

Giese et al.

[11] Patent Number: 5,795,910

[45] Date of Patent: Aug. 18, 1998

[54] METHOD AND COMPOSITIONS FOR INHIBITING PROTEIN KINASES

[75] Inventors: Neill A. Giese; Nathalie Lokker, both of San Francisco, Calif.

[73] Assignee: Cor Therapeutics, Inc., So. San Francisco, Calif.

[21] Appl. No.: 332,597

[22] Filed: Oct. 28, 1994

[51] Int. Cl.$^6$ .................................................... A61K 31/335
[52] U.S. Cl. ....................................................... 514/450
[58] Field of Search ............................................ 514/450

[56] References Cited

FOREIGN PATENT DOCUMENTS

| A-251813 | 1/1988 | European Pat. Off. . | |
| 0 606 044 A1 | 7/1994 | European Pat. Off. | 514/449 |
| 62-39523 | 2/1987 | Japan . | |
| 62-39558 | 2/1987 | Japan . | |
| 62-42923 | 2/1987 | Japan . | |
| 62-42925 | 2/1987 | Japan . | |

OTHER PUBLICATIONS

Arch. Geschwulstforsch., vol. 53, No. 1, 1983, pp. 9–15, XP000568651, R. Thust et al.: "Genotoxicity of Fusarium mycotoxins (nivalenol, fusarenon-x, t–2 toxin and zearalenone) in chinese hamster V79–E cells in vitro."

Proc. Annu. Meet. Am. Assoc. Cancer Res., vol. 35, 1994, p. 88, XP002001543, D.T. Zava et al.: "Effects of plant and fungal estrogens on E-sensitive human breast cancer cells." abstract #525.

Cell, vol. 69, No. 7, 1992, pp. 1227–1236, XP000567055, J. Chung et al.: "Rapamycin–FKBP specifically blocks growth–dependent activation of and signalling by the 70kd S6 protein kinases."

Food Chem. Toxicol., vol. 21, No. 6, 1983, pp. 779–783, XP000568648, R.G. Arora et al.: "Inhibition of ochratoxin A teratogenesis by zeraralenone and diethylstilbestrol."

Gal et al., (1952) "Studies on the Biological Action of Malononitriles: I. The Effect of Substituted Malononitriles on the Growth of Transplanted Tumors in Mice." *Cancer Research*, 12:565–73.

Kuiper–Goodman et al., (1987) "Risk Assessment of the Mycotoxin Zearalenone." *Regulatory Toxicology and Pharmacology*, 7:253–306.

Bennett et al., (1974) "Use of the Anabolic Agent Zearanol (Resorcyclic Acid Lactone) as a Growth Promoter for Cattle." *The Veterinary Record*, 94:235–239.

Willemart et al., (1983) "A Ral Compound as an Anabolic in Cattle." *Veterinary Research Communications*, 7:35–44.

Roche et al., (1983) "Resorcylic Acid Lactone as an Anabolic Agent in Cattle." *Veterinary Research Communications*, 7:45–50.

Sheffield et al., (1985) "Zeranol (β–Resorcyclic Acid Lactone), A Common Residous Component of Natural Foodstuffs, Stimulates Developmental Growth of the Mouse Mammary Gland." *Cancer Letters*, 28:77–83.

Mastri et al., (1985) "In Vivo Oestrogenicity and Binding Characteristics of α–Zearalanol (P–1496) to Different Classes of Oestrogen Binding Proteins in Rat Liver." *J. Steroid Biochem*, 23(3):279–289.

Edwards et al., (1989) "Murine Macrophage Activation with Resorcyclic Acid Lactones (RALs): Comparison with Diethylstilbestrol and 17β–Estradiol." *Immunopharmacology*, 17:107–118.

Katzenellenbogen et al., (1979) "Zearalenones: Characterization of the Estrogenic Potencies and Receptor Interactions of a Series of Fungal β–Resorcylic Acid Lactones." *Endocrinology*, 105:33–40).

*Primary Examiner*—Jerome D. Goldberg
*Attorney, Agent, or Firm*—Cooley Godward LLP

[57] ABSTRACT

A method for selectively inhibiting a kinase is disclosed, which comprises contacting a composition containing a kinase with a molecule of the formula

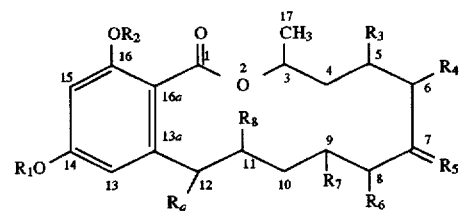

wherein $R_1$ is H, lower alkyl, or lower alkanoyl; $R_2$ is H, lower alkyl, or lower alkanoyl; $R_3$ and $R_4$ together represent a cis double bond or —O— or each of $R_3$ and $R_4$ independently represents H or OR; $R_5$ is =O, =S, or —H, —OR; $R_6$ and $R_7$ together represent a double bond or —O— or each of $R_6$ and $R_7$ independently represents H or OR; $R_4$ and R together represent a double bond or —O— or each of $R_8$ and $R_9$ independently represents H or OR; and each R independently represents H, lower alkyl, or lower alkanoyl.

28 Claims, 1 Drawing Sheet

METHOD AND COMPOSITIONS FOR INHIBITING PROTEIN KINASES

FIELD OF THE INVENTION

This invention relates to inhibitors of protein kinases, especially tyrosine kinases, and to uses thereof in the analysis of kinases and their substrates and in the inhibition of processes dependent on kinases, such as cell growth.

BACKGROUND

Tyrosine-specific protein kinases (tyrosine kinases) represent a family of enzymes which catalyze the transfer of the terminal phosphate of adenosine triphosphate to tyrosine residues in protein substrates. The first members of this class to be identified were tyrosine kinases associated with viral genes (termed oncogenes) which were capable of cell transformation (i.e. pp60v-src and pp98v-fps). Later it was shown that there were normal cellular counterparts (i.e. pp60c-src and pp98c-fps) to these viral gene products. A third category of tyrosine kinases to be identified are those termed the growth factor receptors, which includes insulin, epidermal growth factor (EGF), platelet derived growth factor (PDGF), fibroblast growth factor (FGF), and p185HER-2 receptors. All of these tyrosine kinases are believed, by way of substrate phosphorylation, to play critical roles in signal transduction for a number of cell functions.

Though the exact mechanisms of signal transduction have yet to be elucidated, tyrosine kinases have been shown to be important contributing factors in cell proliferation, carcinogenesis and cell differentiation.

Cell replication can be triggered by the exposure of cells to one or more growth factors, examples of which are FGF, EGF, and PDGF. Such growth factors specifically interact with their corresponding receptors, which receptors comprise an extracellular domain, a transmembrane domain and a cytoplasmic domain which possesses the tyrosine kinase enzymatic activity. The initiation of cellular proliferation is believed to occur when a growth factor binds to the extracellular domain of its receptor at the cell surface. This growth factor-receptor binding induces receptor dimerization which results in receptor autophosphorylation, an increase in enzymatic activity of the receptor and substrate phosphorylation. Recently, a common pathway for signaling from the cell surface to the nucleus has been identified and shown to be utilized by the tyrosine kinase growth factor receptors. This pathway involves the growth factor mediated activation of the ras protein which initiates a protein kinase cascade that leads to the phosphorylation of transcriptional factors that regulate the expression of genes involved in cell division.

Receptor autophosphorylation and the phosphorylation of intracellular substrates are biochemical events which are required for growth factor signaling and cell proliferation. This has been demonstrated by eliminating the protein tyrosine kinase activity of a number of receptors including the EGF receptor, the FGF receptor and the PDGF receptor by site-directed mutagenesis which results in the complete loss of the receptors biological activity. Also, protein kinase inhibitors such as staurosporin, K252a and the tyrphostins which block receptor tyrosine kinase enzymatic activity prevent intracellular signaling and cell proliferation. These studies confirm the essential role of tyrosine phosphorylation in signaling by the growth factor receptors and demonstrate that compounds that inhibit tyrosine kinase activity can be used to regulate cell proliferation.

Many disease states are characterized by uncontrolled cell proliferation. These diseases involve a variety of cell types and include disorders such as cancer, psoriasis, pulmonary fibrosis, glomerulonephritis, atherosclerosis and restenosis following angioplasty. The utility of tyrosine kinase inhibitors for the treatment of such disorders has been demonstrated in a number of in vivo studies. Tyrosine kinase inhibitors with selectivity for the EGF receptor family have been shown to block tumor formation in animals, thus demonstrating their potential usefulness for directly suppressing tumor cell growth in the treatment of human cancer, especially breast carcinoma. Also, tumor metastasis and its associated angiogenesis has been shown to be inhibited by preventing the activation of the vascular endothelial growth factor (VEGF) receptor tyrosine kinase which indicates a utility for tyrosine kinase inhibitors in blocking separate events that occur during carcinogenesis.

In experimental models of glomerulonephritis, a 20-fold increase in the PDGF receptor expression is associated with mesangial cell proliferation. Neutralization of PDGF which prevents the activation of its tyrosine kinase receptor limits the amount of renal degeneration which normally occurs. These studies demonstrate that a tyrosine kinase inhibitor which blocks the PDGF receptor could have potential for the treatment of human glomerulonephritis.

One major unsolved problem of interventional cardiology is restenosis following coronary angioplasty. Of the nearly 400,000 angioplasties currently performed in the United States each year, 30–40% fail within the first year due to restenosis. The process of restenosis involves the reocclusion of an atherosclerotic artery which in many cases is due to the proliferation of smooth muscle cells which is mediated by growth factors such as PDGF and FGF. In animal models of restenosis, antibodies which block the activation of PDGF or FGF receptor tyrosine kinase activity prevent smooth muscle cell proliferation and the formation of neointima. These studies indicate that tyrosine kinase inhibitors that block PDGF or FGF receptor function could have utility in treating human restenosis.

Currently the chemotherapy of cancer makes use of inhibitors of DNA synthesis (e.g. adriamycin, fluorouracil) and compounds which disrupt the cytoskeleton (vinblastine). These compounds are highly toxic since their inhibitory activity is not limited to cancer cells, with the distinction, however, that tumor cells are more readily attacked by the aforesaid inhibitors because these cells divide more rapidly and their DNA metabolism is consequently more active. A few types of cancers are treated with specific hormone derivatives. These cases, however, are the exception and the chemotherapeutic treatment for the majority of the various types of cancer is non-specific.

In the early 1980's it became apparent that 20 to 30 percent of cancers express characteristic oncogenic products which are growth factor receptors or their mutated homologs, and which exhibit PTK activity. The PTK activity is intrinsic to the receptor or its oncogene homolog and influences the cell proliferation via its PTK domain. Furthermore, each of these receptors (normal or mutated) exhibits a characteristic PTT activity with a distinct substrate specificity. One of these receptors is the epidermal growth factor (EGF) receptor and its oncogenic homolog V-ERB-B.

As a result of the above-described developments regarding the PTK activity of growth factor receptors, it has been proposed to treat cancer by means of various chemical substances capable of inhibiting the PTK activity of EGF. See, for example, Japanese patent Nos. 62-39523, 62-39558, 62-42923 and 62-42925. For example, aforementioned Japanese Laid-open Patent No. SHO 62-39558 discloses alpha-cyano-2,5-dihydroxycinnamamide as the active compound in compositions effective as PTK inhibitors.

The use of cinnamyl malononitrile and various benzylidene malononitrile compounds as tumor growth inhibitors is disclosed in Gal et al., Studies on the Biological Action of Malononitriles. I. The Effect of Substituted Malononitriles on the Growth of Transplanted Tumors in Mice, Cancer Research, 12:565-72, 1952.

SUMMARY OF THE INVENTION

Accordingly, it is an object of the present invention to provide new and useful formulations of kinase inhibitors.

It is further an object of the present invention to provide additional uses for old compositions of recognized low toxicity.

These and other objects of the invention have been accomplished by providing a method for inhibiting a protein kinase, which comprises contacting a composition containing said kinase with a molecule of the formula (I) below:

wherein:

$R_1$ is H, lower alkyl, or lower alkanoyl;

$R_2$ is H, lower alkyl, or lower alkanoyl;

$R_3$ and $R_4$ together represent a cis double bond or —O— or each of $R_3$ and $R_4$ independently represents H or OR;

$R_5$ is =O, =S, or —H, —OR;

$R_6$ and $R_7$ together represent a double bond or —O— or each of $R_6$ and $R_7$ independently represents H or OR;

$R_8$ and $R_9$ together represent a double bond or —O— or each of $R_8$ and $R_9$ independently represents H or OR; and each R independently represents H, lower alkyl, or lower alkanoyl.

The present invention is also directed to pharmaceutical compositions for the control of kinase dependent diseases in mammals which comprise a compound of formula (I) in a pharmaceutically acceptable carrier and to a method of controlling kinase dependent diseases which comprises administering to a mammal suffering from kinase dependent diseases a kinase dependent disease controlling amount of a compound of the formula shown above. Here "mammal" has the usual meaning and includes humans in addition to other mammals. Pharmaceutical uses are intended to include veterinary uses, especially use in domesticated animals such as cattle, sheep, pigs, goats, dogs, cats, rabbits, hamsters, gerbils, rats, and mice.

Other features and advantages will be apparent from the specification and claims.

DESCRIPTION OF THE DRAWINGS

The invention will be better understood by reference to the following detailed description in combination with the figures that form part of this specification, wherein.

DESCRIPTION OF SPECIFIC EMBODIMENTS

The present invention is directed to a new use of previously known compounds as well as to certain compounds related to previously known compounds that are identified here for the first time. The compounds are related to zeaenol and are macrolides, containing a 14-membered ester ring fused to a catechol ring. Compounds of this class have been known for over 25 years, having been used principally as cattle feed additives. See, for example, Kuiper-Goodman et al., "Risk Assessment of the Mycotoxin Zearalenone", Regulatory Toxicology and Pharmacology 7:253–306 (1987); Bennett et al., "Use of the Anabolic Agent Zearnol (Resorcylic Acid Lactone) as a Growth Promoter for Cattle", The Veterinary Record, pp. 235–239 (Mar. 16, 1974); Willemart et al., "A RAL Compound as an Anabolic in Cattle", Veterinary Research Communications 7:35–44 (1987); and Roche et al., "Resorcylic Acid Lactone as an Anabolic Agent in Cattle", Veterinary Research Communications 7:45–50 (1983). Other known activities of these compounds are as estrogenic agents. See, for example, Sheffield et al., "Zeranol β-Resorcylic Acid Lactone), A Common residous Component of Natural Foodstuffs, Stimulates Developmental Growth of the Mouse Mammary Gland", Cancer Letters, 28:77–83 (1985); Mastri et al., "In Vivo Oestrogenicity and Binding Characteristics of α-Zearalanol (P1496) to Different Classes of Oestrogen Binding Proteins in Rat Liver", J. Steroid Biochem. 23(3) :279–289 (1985); Edward et al., "Murine Macrophage Activation with Resorcyclic Acid Lactones (RALs): Comparison with Diethylstilbestrol and 17β-Estradiol", Immunopharmacology 17:107–118 (1989); and Katzenellenbogen et al., "Zearalenones: Characterization of the Estrogenic Potencies and Receptor Interactions of a Series of Fungal β-Resorcylic Acid Lactones", Endocrinology 105:33–40 (1979). However, they have not previously been used or known to be useful as inhibitors of kinase, an important biochemical control molecule. In general, the compounds have the formula wherein:

$R_1$ is H, lower alkyl, or lower alkanoyl;

$R_2$ is H, lower alkyl, or lower alkanoyl;

$R_3$ and $R_4$ together represent a cis double bond or —O— or each of $R_3$ and $R_4$ independently represents H or OR;

$R_5$ is =O, =S, or —H, —OR;

$R_6$ and $R_7$ together represent a double bond or —O— or each of $R_6$ and $R_7$ independently represents H or OR;

$R_8$ and $R_9$ together represent a double bond or —O— or each of $R_8$ and $R_9$ independently represents H or OR; and each R independently represents H, lower alkyl, or lower alkanoyl.

It has now been discovered that these compounds and pharmaceutical compositions containing them can be used to bind with and inhibit kinase. Such uses are described below in more detail.

Definition of terms

As employed above and throughout the disclosure, the following terms, unless otherwise indicated, shall be understood to have the following meanings:

"Alkyl" means a saturated aliphatic hydrocarbon which may be either straight- or branch-chained containing from about 1 to about 6 carbon atoms.

"Lower alkyl" means an alkyl group as above, having 1 to about 4 carbon atoms which may be straight- or branch-chained such as methyl, ethyl, propyl, isopropyl, butyl, isobutyl, sec-butyl or tert-butyl. Halogenated alkyl groups, particularly fluorinated alkyl groups, such as $CF_3$, $CH_2CF_3$, and $CF_2CF_3$, are included within the definition of alkyl groups.

"Alkoxy" means an alkyl-oxy group in which "alkyl" is as previously described. Lower alkoxy groups are preferred. Exemplary groups include methoxy, ethoxy, n-propoxy, i-propoxy and n-butoxy.

"Acyl" means an organic radical derived from an organic acid, a carboxylic acid, by the removal of its acid hydroxyl group. Preferred acyl groups are lower alkyl carboxylic acid groups such as acetyl and propionyl. Benzoyl is also preferred.

"Halo" means a halogen atom. Preferred halogens include chloride, bromide and fluoride.

Structure

Exemplary structures are set out in the table below. Example compound 1 in this table is compound 292 in the Examples section of this specification.

figurations of the individual chiral centers are preferably those in which the chiral centers have the same relative configurations as found in one or another of the naturally occurring resorcyclic acid derivatives (and thus are most easily prepared by synthetic modifications). However, synthetic techniques are available for inverting chiral centers (e.g., $SN_2$ displacement reactions), and such techniques can be used to prepare non-naturally occurring isomers where such isomers are desired. When a particular stereochemistry is desired at a given location, numerous techniques are available for either stereospecific synthesis or for synthesis of diastereomers, since the introduction of a single chiral center (or pair of chiral centers) in a molecule already containing a chiral center (such as the chiral center at C3) results in the production of diastereomers (rather than enantiomers) that can be separated by normal physical techniques. Two preferred chiral center orientations are those in which the carbon at position 8 has an S configuration and the carbon at position 9 has an S configuration when OH groups are present at both locations and those in which the carbon at position 3 has an S configuration.

In any event, the presence of mixtures of diastereomers generally will not detract from the invention, as the presence of inactive diastereomers (if any) mere acts in the same manner as the presence of any other inactive material (such as a pharmaceutical carrier).

TABLE 1

| | R | | | | | | | | |
|---|---|---|---|---|---|---|---|---|---|
| Ex. | 1 | 2 | 3 | 4 | 5 | 6 | 7 | 8 | 9 |
| 1 | Me | H | = | = | O | OH | OH | = | = |
| 2 | MeCO | Me | —O— | —O— | O | OH | OH | = | = |
| 3 | H | H | = | = | O | —O— | —O— | = | = |
| 4 | Me | H | = | = | O | OH | OH | OH | OH |
| 5 | Me | H | = | = | O | OH | OH | H | H |
| 6 | Me | H | = | = | O | H | H | = | = |
| 7 | Me | H | = | = | H,OH | H | H | H | H |
| 8 | CF$_3$CO | Et | = | = | S | H | H | = | = |
| 9 | MeCO | MeCO | —O— | —O— | S | H | H | = | = |
| 10 | H | i-Pr | OH | OH | S | OH | OH | = | = |
| 11 | H | H | H | H | O | H | H | H | H |
| 12 | H | H | OH | OH | O | OH | OH | OH | OH |
| 13 | H | H | OMe | OMe | O | OH | OH | = | = |
| 14 | t-Bu | CF$_3$ | = | = | O | OH | OH | = | = |
| 15 | H | H | = | = | S | OBu | OH | OH | OH |
| 16 | MeCO | H | OH | OH | O | OH | OCOMe | OMe | OMe |
| 17 | iPnCO | Me | = | = | S | = | = | OH | OH |

Footnotes to Table
= (in adjacent columns) represents double bond between adjacent indicated carbons
—O— (in adjacent columns) represents epoxide between adjacent indicated carbons
Me—methyl; Et—ethyl; Pr—n-propyl; iPr—iso-propyl; Bu—n-butyl; sBu—sec-butyl; iBu—iso-butyl; tBu—tert-butyl; 1Pn—1-pentyl; 2Pn—2-pentyl; 3Pn—3-pentyl; 2MB—2-methylbutyl; iPn—iso-pentyl (3-methylbutyl); nPn—neo-pentyl (2,2-dimethylpropyl); 11MP—1,1-dimethylpropyl; 12MP—1,2-dimethylpropyl; MeCO—acetyl (remaining acyl derivatives named in same manner)

Stereochemistry of chiral centers and geometry of double bonds

The compounds used in the method of the invention can contain up to 3 C—C double bonds —$R_3$–$R_4$, $R_6$–$R_7$, and $R_8$–$R_9$. The $R_3$–$R_4$ double bond, when present, must be cis in order for the resulting molecule to be active in the manner indicated. The $R_6$–$R_7$ and $R_8$–$R_9$ double bonds, when present, are preferably trans.

Potential chiral centers exist at carbons 3, 5, 6, 8, 9, 11, and 12 (macrolide numbering system; see formula I). Since stereochemical designations (R and S) vary depending on the nature of the substituent at a given location, the preferred stereochemistry of a particular location will be R or S, depending on the substituent. Absolute stereochemical con- Preparation and production of compounds The compounds used in the invention are resorcyclic acid lactones and can be prepared and modified by known techniques. Some of these compounds are available as biological products of fermentation, and others can be obtained by chemical modification of the initial biologic products. Biologic production of compound 1 in Table 1 is described in the examples below. Other biologic and chemical synthetic techniques are described in a number of U.S. patents, including U.S. Pat. Nos. 3,373,030, 3,551,454, 3,810,918, 3,836,544, and 3,925,423, all of which are herein incorporated by reference. The last of these patents is particularly useful as it gives a general synthesis for making compounds of the invention from readily available starting materials.

For example, trans-zearalenone can be obtained by the cultivation of the microorganism Gibberella zeae (Gordon) using a suitable fermentation method, as described for example in U.S. Pat. No. 3,196,019. By way of example, the unsaturated carbon bond in the lactone zearalenone ring can be hydrogenated according to the procedure of U.S. Pat. No. 3,239,354. The ketone group of zearalenone can be reduced to the corresponding alcohol by the procedure of U.S. Pat. No. 3,239,341 or to a methylene group by the procedure described in U.S. Pat. No. 3,237,341. Replacement of the hydrogen of the hydroxy groups by an alkyl, alkanoil, aryl, or arylalkyl group is disclosed in U.S. Pat. Nos. 3,239,342 and 3,239,347. Cis-trans conversion of double bonds using irradiation at 2800–3500 Angstroms is disclosed in U.S. patent application No. 317,117, filed Dec. 21, 1972, now abandoned. Separation of diastereomers of zearalanol is disclosed in U.S. Pat. No. 3,687,982. All of these patent documents are herein incorporated by reference, as examples of the existing state of the art of synthetic production of compounds useful in the present invention.

Various substituents on the phenyl or macrolide ring can be present in the starting compound or added after formation of the condensation product by methods known in the art for substitution or conversion of one group to another. If the substituents themselves are reactive, then the substituents can themselves be protected according to the techniques known in the art. A variety of protecting groups known in the art may be employed. Examples of many of these possible groups may be found in "Protective Groups in Organic Synthesis" by T. W. Green, John Wiley and Sons, 1981. Primary alcohols can be oxidized by oxidizing agents known in the art to form carboxylic acids or aldehydes and secondary alcohols can be oxidized to form ketones. Thus, substitution or alteration reactions can be employed to provide a variety of substituents throughout the molecule of the starting material, intermediates or the final product.

Examples of scientific publications that give details of biologic and synthetic techniques for preparing compounds of the invention include the follow, all of which are herein incorporated by reference:

Sugawara et al., "Zearalenone Derivatives Produced by the Fungus Drechslera Portulacae", Phytochemistry, 31(6) 1987–1990 (1992).

El Sharkawy et al., "Microbial transformation of Zaeralenone. 2. Reduction, Hydroxylation, and Methylation Products", J. Org. Chem., 53:515–519 (1988).

Agatsuma et al., "Revised structure and Sterochemistry of Hypothemycin", Chem Pharm. Bull. 41(2):373–375 (1993).

Nair et al., "Metobolites of Pyrenomycetes XIII:[1] Structure of (+) Hypothemycin, an Antibiotic Macrolide from *Hypomyces trichothecoides*", Tetrahedron Letters, 21:2001–2012 (1980).

Ellestad et al., "New Zearalenone Related Macrolides and Isocoumarins from and Unidentified fungus", J. org. Chem., 43(12):2339–2343 (1978).

Gatenbeck Sten, "The Biosinthesis of Oxytetracycline, Biochemical and Biophysical research Communications", 6(6):422–426 (1961/62).

Ayer et al., "Minor Metabolites of Monocillium Norinii", Phytochemistry, 5:1353–1355 (1987).

Hagler et al., "Identification of Naturally Occurring Isomer of Zearlenol Produced by *Fusarium roseum* 'Gibbosum' in rice Culture", Applied and environmental Microbiology, 37(5):849–853 (May 1979).

Urry et al., "The Structure of Zearlenon", Tetrahedron letters, 27:3109–3114 (1966).

Bollinger et al., "Vier neue Metabolite von *Giberall zeae*: 5-Formyl-zearalenon, 7'-Dehydrozearalenon, 8'-Hydroxy- und 8'-epi-Hydroxy-zeara-lenon", Helvetica Chimica* Acta, 55(8):305–306 (1972).

Ayer et al., "The Isolation, Identification, and Bioassay of the Antifungal Metabolites Produced by *Monocillium nordinii*", Can. J. Microbiol. 26:766–773 (1980).

Mirrington et al., "The Constitution of Radicicol", The Tetrahedron Letters 7:365–370 (1964).

Shipchandler T. Mohammed, "Chemistry of Zearalenone and some of its Derivatives", Heterocycles, 3(6)471–520 (1975).

Kuo et al., "The resolution of (±)-Zearalenone. Determination of the Absolute Configuration of the Natural Enantiomorph", Chemical Communications pp. 761–762 (1967), and McCpra et al., "The Constitution of Monorden, an Antibiotic with Tranquilising Action", Tetrahedron Letters 15:869–875 (1964).

Use as inhibitors of kinases

The compounds of this invention are all readily adapted to therapeutic use as kinase inhibitors for the control of kinase dependent diseases in mammals, especially those related to tyrosine kinase. The ability of a resorcyclic acid derivative to specifically inhibit one of the three types of protein kinases in preference to other classes (the three known classes are discussed below) is one of the factors that determines the manner in which a specific compound will be used. Tyrosine kinase dependent diseases include hyperproliferative disorders which are initiated/maintained by aberrant tyrosine kinase enzyme activity. Examples include cancer, atherosclerosis, and antiangiogenesis (e.g., tumor growth, diabetic retinopathy). Although there is less information available on the relationship of other classes of kinases to specific diseases, it is understood in the art that therapeutically useful protein tyrosine kinase (PTK) inhibiting compounds preferably should be selective, and the same is true for the other classes of kinases. The PTK inhibitors quercetin, genistein, and staurosporin inhibit many other protein kinases in addition to tyrosine kinases and as a result of their lack of specificity are highly cytotoxic. Therefore, routine assays which measure cytotoxicity can be used identify PTK inhibitors (or inhibitors of other classes of kinases) which are likely to produce undesired side effects due to a lack of selectivity.

Three general classes of protein kinases have been identified based upon the amino acid(s) that serves as their substrate: kinases that phosphorylate tyrosine, kinases that phosphorylate tyrosine and threonine and kinases that phosphorylate serine and threonine. As a more detailed test of selectivity, compounds should be tested for their ability to inhibit the enzymatic activity of a range of these protein kinases. Tyrosine specific protein kinases are described in the Background section. Examples of kinases that phosphorylate serine and threonine (the most common class) include RAF, protein kinase A, protein kinase C, and TGF beta receptor. The kinase MEK is an example of kinases that phosphorylate tyrosine and threonine.

In the following discussion of uses of kinase inhibitors, the discussion focuses on tyrosine kinases, since these are the kinase that have been most readily accessible to pharmaceutical control. It should be understood, however, that any discussion here of use of a compound as a tyrosine kinase inhibitor is equally applicable to use of a compound that is specific for one of the other kinase classes, once the specificity of action is known. Whether a resorcyclic compound is specific for a particular class of kinase is readily determined by use of the kinase activity assays set out in the examples (or an otherwise identical assay that substitutes a different kinase for the kinase discussed in the example). In order to avoid undue repetition, the following discussion discusses tyrosine kinases as examples of what can be done with other classes of kinases. Thus a reference to "tyrosine kinase" or "PTK" for a particular use or in a particular situation should be taken as an example of a use of a compound specific for any of the kinase classes, unless otherwise specified or clear from the context.

In order for compounds that inhibit PTK or one of the other kinase classes to be therapeutically useful they should be active on intact cells. It is known that PTK inhibitors that are identified on the basis of their ability to inhibit isolated enzyme preparations are often weak or ineffective at inhibiting native PTKs. This lack of activity is due either to the inability of the PTK inhibitors to get across the cell membrane to reach their site of action or they are unable to inhibit PTKs in cells where adenosine triphosphate (ATP) concentrations are high and other factors may be involved. Several methods are readily available for determining the activity of PTK inhibitors against growth factor receptor tyrosine kinases on intact cells. Growth factor treatment of cells results in the rapid autophosphorylation of the corresponding receptor as well as phosphorylation of the receptors substrates and these events can be measured using antiphosphotyrosine antibodies. Also, additional intracellular signaling events can be measured including calcium flux, inositol phosphate metabolism and cellular DNA synthesis. Finally, a therapeutically useful PTK inhibitor must be able to block cellular proliferation which is the unwanted outcome of growth factor action and is easy to monitor.

It is theorized that solubility of the compounds of the present invention both in water and in mildly hydrophobic solvents will enhance the probability that they traverse the cell membrane. Various insoluble compounds, however, have exhibited significant kinase inhibition in in vitro testing.

Compounds of this invention may be useful in the form of the free acid, in the form of a salt and as a hydrate. All forms are within the scope of the invention. Basic salts may be formed and are simply a more convenient form for use; in practice, use of the salt form inherently amounts to use of the acid form. The bases which can be used to prepare the salts include preferably those which produce, when combined with the free acid, pharmaceutically acceptable salts, that is, salts whose anions are non-toxic to the animal organism in pharmaceutical doses of the salts, so that the beneficial properties inherent in the free acid are not vitiated by side effects ascribable to the cations. Although pharmaceutically acceptable salts of the acid compound are preferred, all salts are useful as sources of the free acid form even if the particular salt per se is desired only as an intermediate product as, for example, when the salt is formed only for purposes of purification and identification, or when it is used as an intermediate in preparing a pharmaceutically acceptable salt by ion exchange procedures.

Compounds within the scope of this invention that have activity as specific inhibitors as protein tyrosine kinase inhibitors possess therapeutic value as cellular antiproliferative agents for the treatment of certain conditions including, for example, psoriasis and restenosis. It is expected that the invention will be particularly applicable to the treatment of atherosclerosis. With regard to the treatment of some conditions, for example, atherosclerosis, certain people may be identified as being at high risk, for example, due to genetic, environmental or historical factors. Compounds within the scope of the present invention can be used in preventing or delaying the occurrence or reoccurrence of such conditions or otherwise treating the condition.

Compounds of the present invention can be administered to a mammalian host in a variety of forms i.e., they may be combined with various pharmaceutically acceptable inert carriers in the form of tablets, capsules, lozenges, troches, hard candies, powders, sprays, elixirs, syrups, injectable or eye drop solutions, and the like depending on the chosen route of administration, e.g., orally or parenterally. Parenteral administration in this respect includes administration by the following routes: intravenous, intramuscular, subcutaneous, intraocular, intrasynovial, transepithelial (including transdermal, ophthalmic, sublingual and buccal), topical (including ophthalmic, dermal, ocular, rectal, nasal inhalation via insufflation and aerosol), and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 1 and 1000 mg of active compound.

The tablets, troches, pills, capsules and the like may also contain the following: a binder such as polyvinylpyrrolidone, gum tragacanth, acacia, sucrose, corn starch or gelatin; an excipient such as calcium phosphate, sodium citrate and calcium carbonate; a disintegrating agent such as corn starch, potato starch, tapioca starch, certain complex silicates, alginic acid and the like; a lubricant such as sodium lauryl sulfate, talc and magnesium stearate; a sweetening agent such as sucrose, lactose or saccharin; or a flavoring agent such as peppermint, oil of wintergreen or cherry flavoring. Solid compositions of a similar type are also employed as fillers in soft and hard-filled gelatin capsules; preferred materials in this connection also include lactose or milk sugar as well as high molecular weight polyethylene glycols. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, flavoring such as cherry or orange flavor, emulsifying agents and/or suspending agents, as well as such diluents as water, ethanol, propylene glycol, glycerin and various like combinations thereof. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. For purposes of parenteral administration, solutions in sesame or peanut oil or in aqueous propylene glycol can be employed, as well as sterile aqueous solutions of the corresponding water-soluble, alkali metal or alkaline-earth metal salts previously enumerated. Such aqueous solutions should be suitable buffered, if necessary, and the liquid diluent first rendered isotonic with sufficient saline or glucose. Solutions of the active compound as a free base or a pharmacologically acceptable salt can be prepared in water suitably mixed with a surfactant such as hydroxypropylcellulose. A dispersion can also be prepared in glycerol, liquid polyethylene glycols and mixtures thereof and in oils. Under ordinary conditions of storage and use, these preparations contain a preservative to prevent the growth of microorganisms. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for drop-wise administration to the eye.

The therapeutic compounds of this invention may be administered to a mammal alone or in combination with pharmaceutically acceptable carriers. As noted above, the relative proportions of active ingredient and carrier are determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and, if necessary, will be increased by small increments until the optimum effect under the circumstances is reached. The therapeutic human dosage, based on physiological studies using rats, will generally be from about 0.01 mg to about 100 mg/kg of body weight per day or from about 0.4 mg to about 10 g and higher although it may be administered in several different dosage units from once to several times a day. Oral administration requires higher dosages.

The compounds are administered either orally or parenterally, or topically as eye drops, in dosages ranging from about 0.1 to 10 mg/kg of body weight per day in single or divided doses. Of course, in particular situations, at the discretion of the attending physician, doses outside of this range will be used.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case, the ratio chosen will depend on such factors as the solubility of the active component, the dosage contemplated and the precise route of administration.

The invention now being generally described, the same will be better understood by reference to the following detailed examples, which are provided for the purpose of illustration only and are not to be considered limiting of the invention unless otherwise specified.

EXAMPLES

Example 1. Preparation of Compound 292

Fermentation. C292FE, a Curvularia species, was grown in a petri plate containing growth medium (agar with 4.0 g/L yeast extract, 10.0 g/L malt extract, 4.0 g/L glucose with 0.005 ml/ml trace elements) at 28° C. and 80% humidity. Mycelium was macerated with glass beads in a tube containing 4.5 ml of a solution with 10% glycerol and 5% lactose to form a homogenous suspension. A 250 ml Erlenmeyer flask, containing 30 ml seed medium (20.0 g/L glucose, 15.0 g/L pharmamedia, 3.0 g/L $(NH_4)_2SO_4$, 0.03 g/L $ZnSO_4 \cdot 7H_2O$, 4.0 g/L $CaCO_3$, 5.0 g/L yeast extract, and $H_2O$ to 1 L) was inoculated with 1–2 ml of the macerated mycelium. The seed flask was incubated on a rotary shaker at 28° C. for 2 days at 250 rpm, amplitude 50 mm.

One ml aliquots from the seed flask were transferred to 30 ml fermentation media (60.0 g/L mannitol, 12.5 g/L soybean meal, 2.5 g/L citric acid, 0.5 g/L yeast extract, and $H_2O$ to 1 L), pH 7.0 in 250 ml Erlenmeyer flasks and incubated for 5–6 days on a rotary shaker at similar conditions.

Extraction. For this example, a 15 L fermentation was provided in 250 ml shake flasks, each flask containing 30 ml broth. An aliquot of approximately 15 ml ethyl acetate was added to each flask within 5 minute after removal from the shaker board. The contents of each flask were then combined and the mycelium filtered away from the liquid by suction filtration through a polypropylene filter. The mycelium was taken up in 2 L ethyl acetate and briefly homogenized to break up the cells. The mixture was filtered and the filtrate saved. This procedure was repeated three more times. The aqueous layer was extracted separately in a separatory funnel with 10 L of ethyl acetate. The ethyl acetate layers from the mycelium and aqueous extracts were combined, dried over sodium sulfate and filtered. After removal of the solvent by the rotary evaporation, the resulting residues were dried on the vacuum pump over night. The crude extract yielded 2.565 g.

CPC FRACTIONATION. The crude extract underwent CPC fractionation on a PC, Inc. high speed countercurrent chromatograph containing a "Tripple" coil column. A 1:3:3:3 ratio by volume of n-hexane, ethyl acetate, methanol and water was mixed and allowed to settle overnight. The lower layer was pumped into the CPC column as the stationary phase. The upper layer was used as the mobile phase. The column had a rotation speed of 1,040 rpm and a flow rate of 3 ml per minute was used. The injection size was 400 mg of crude extract dissolved in 5 ml upper and 5 ml lower phase. A photo diode array detector detected the metabolites at 270 nm. An active metabolite eluted at 96 to 114 minutes along with an inactive isomer. These fractions were combined with those from five additional CPC fractionations to give 75.6 mg of the mixture of the two metabolites.

HPLC Fractionation. The mixture obtained above was subjected to HPLC fractionation using the following conditions: analytical $C_{18}$-column (8×100 mm, Waters, Novapak); flow rate; 1 mL/min.; 0.5 mg dissolved in 10 ml of dimethylsulfoxide (DMSO) per injection; monitored at 270 nm; initial conditions; 70% water/ 30% acetonitrile to 100% acetonitrile over 80 min. applying a linear gradient; peak 1 (inactive metabolite) eluted at 16.90 min. and peak 2 (active metabolite) eluted at 18.74 min.

Conversion and Separation of isomers. C292FE produced two metabolites which differed only in the geometry of one of the two double bonds in the macrocycle. 167 mg obtained from CPC fractionation were dissolved in DMSO at a concentration of 1 mg/ 10 mL. Aliquots of 50 mL (5 mg) were then fractionated by HPLC (Resolve 25 cm×100 cm, 5 mL) in order to separate the isomers. Initial column conditions were 35% methanol/ 65% water. A linear gradient over a period of 25 minutes was applied to the final condition of 90% methanol/ 10% water using a flow rate of 8 ml/min. Under these conditions, the trans isomer (inactive) eluted at 11.3 minutes followed by the cis isomer (active) at 12.2 minutes. Each peak was collected separately and dried by rotary evaporation. The first round of HPLC fractionations yielded 11.7 mg of the cis isomer and 63 mg of the trans isomer. The cis isomer was tested for purity using proton NMR spectroscopy while the trans isomer was resuspended in methanol at a concentration of 5 mg/1.5 mL. This solution was placed in a quartz container and irradiated with ultraviolet light for 35 minutes (Rayonet Photochemical Reactor low pressure Hg lamp). After irradiation, the solution was dried by rotary evaporation, resuspended in DMSO (1 mg/10 mL), and subjected to another round of HPLC fractionations using the conditions described above. This process was repeated until all of the trans isomer was used. The total yield of the cis isomer was 24 mg. The complete structure of this compound (C292) is set out below.

EXAMPLE 2. Inhibition of Protein Kinase Enzymatic Activity by Compound 292

The stimulation of cell proliferation by growth factors such as PDGF, FGF and EGF is dependent upon their induction of autophosphorylation of each of their respective receptor's tyrosine kinases. Therefore, the ability of a PTK inhibitor to inhibit cellular proliferation induced by these growth factor is directly correlated with its ability to block receptor autophosphorylation. To measure beta PDGF receptor autophosphorylation, the Chinese hamster ovary cell line, HR5, was used which had been engineered to stably overexpress the transfected cDNA which encodes the human beta PDGFR. These cells were seeded at 10,000 cells/well in microtiter plates (Falcon 96 well plates) and incubated at 37° C. in RPMI (Gibco BRL) with 10% fetal bovine serum for 3 days at which time confluency was reached. The media was removed from the wells and replaced with 100 ml of serum-free RPMI, and incubation was continued at 37° C. for 18 hours. Compounds (0.01–30 uM) were added to the wells 15 minutes prior to the addition of PDGF BB (100 ng/ml) and the incubation was continued at 37° C. for 10 minutes. The media was drained and 50 ml of freshly prepared lysis buffer (20 mM Tris at pH 7.3, 150 mM NaCl, 1% Triton X-100, 1 mM PMSF, 1 mM sodium orthovanadate, 10 mg/ml aprotinin and 10 mg/ml leupeptin) was added to each well and the plate was shaken vigorously to prepare the cell lysate. The lysates were then cleared by centrifugation at 2600 rpm for 10 min prior to their analysis.

In a separate microtiter plate, monoclonal antibody 1B5B11 directed against the beta PDGF receptor extracellular domain was immobilized by incubating 0.5 mg of antibody per well at 4° C. for 18 hours in 23 mM Tris at pH 8.0, 68 mM NaCl, 14 mM ammonium bicarbonate and 0.01% sodium azide. After antibody immobilization, the wells were blocked with 25 mM N-2-hydroxyethyl) piperazine-$N^1$-(2-ethane sulfonic acid) (HEPES) pH 7.6, 100 mM NaCl, and 0.2% Tween 20 just prior to the addition of cell lysate that had been diluted 1:2 in binding buffer (blocking buffer with 0.3% gelatin). The cell lysate was incubated with immobilized antibody against beta PDGF receptor for 2 hours at room temperature and wells were washed 3 times with 200 ml of wash buffer (PBS, 0.01% Tween 20). To detect the level of beta PDGF receptor phosphorylation, a rabbit anti-phosphotyrosine antibody Upstate Biotechnology, Inc. (UBI) was added at 1.25 mg/ml and incubated for 1 hour at 37° C. After removal of the anti-phosphotyrosine antibody the plates were incubated with goat horseradish conjugated anti-rabbit IgG (Boehringer Mannheim) at 1:1000 dilution prior to the addition of peroxidase substrate (ABTS™). Product formation was monitored at 650 nm using a microtiter plate reader (Molecular devices).

EGF receptor autophosphorylation was measured in MDA MB 468 cells (ATCC# HIB 132), a human mammary tumor cell line that overexpresses the EGF receptor. These cells were grown to confluency in 6-well plates and incubated in serum-free Dulbecco's Modified Eagle Medium (DMEM) medium for 18 hours. The cells were exposed to various concentrations of compounds for 15 minutes and then to EGF (100 ng/ml) for 10 minutes at 37° C. The cells were scraped and lysates were prepared in the same buffer as described for HR5 cells prior to fractionation by conventional SDS PAGE followed by Western blot analysis. For this, proteins were transferred onto nitrocellulose and the membrane was blocked in Tris buffer saline, pH 7.0, 0.1% Tween 20, 5% dry milk. The membrane was blotted with anti-phosphotyrosine antibody (UBI, 1 ug/ml) in binding buffer (TBS, 0.1% Tween 20; 1% dry milk) for 2 hours at room temperature. Detection was performed using a goat anti-rabbit-horseradish peroxidase conjugated IgG (Boehringer Mannheim). The blot was developed using a chemiluminescent system (Amersham).

In order to measure FGF receptor-1 autophosphorylation, the human FGF receptor-1 cDNA was stably over-expressed in CHO cells using standard techniques. These cells were grown to confluency in RPMI with 10% fetal bovine serum, the media was replaced with serum-free RPMI and incubation continued for 18 hours prior to stimulation with BFGF (75 ng/ml) for 10 min at 37° C. in the absence of presence or PTK inhibitors in a concentration range of 0.1–30 uM. Cell lysates were prepared under the same conditions as described above for the EGF receptor assay. Lysates were incubated with a monoclonal antibody directed against the FGF receptor-1 extracellular domain (prepared at COR Therapeutics, South San Francisco, Calif.) and the immunoprecipitated receptor was subjected to SDS-PAGE and Western blot analysis with antiphosphotyrosine antibodies as described above for EGF receptor.

Figure 1:
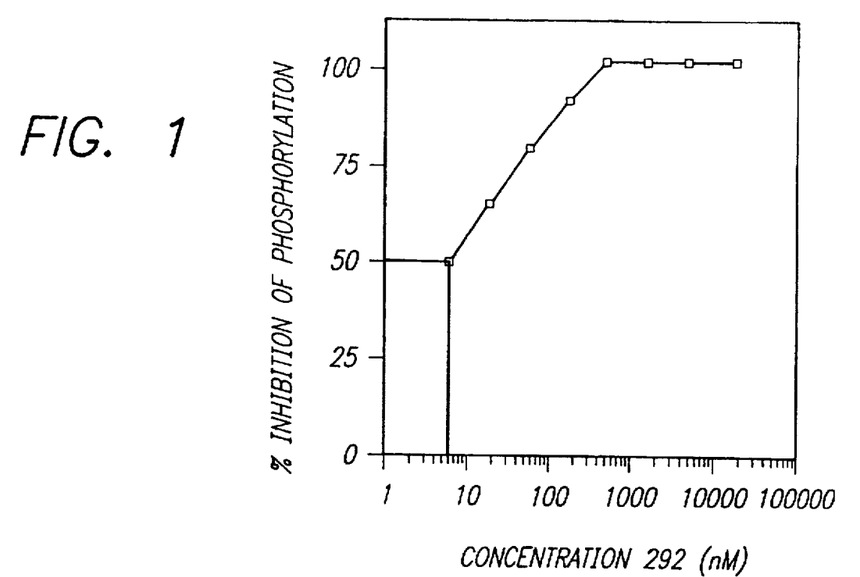
FIG. 1 shows the effect of compound 292 on Beta PDGFR autophosphorylation in HR5 cells.

As shown in FIG. 1, compound 292 efficiently blocked beta PDGF receptor autophosphorylation with an $IC_{50}=6.2$ nM and complete inhibition was observed at concentrations>200 nM. These results were confirmed by SDS-PAGE and Western blot analysis of HR 5 cell lysates using antiphosphotyrosine antibodies (data not shown). Staurosporin is the most potent PDGF receptor tyrosine kinase inhibitor previously described. When direct comparison was made, 292 was found to be 10-fold more potent than staurosporin and 45-fold more potent than the staurosporin analog, K252a (see Table 2 below). These results demonstrate that 292 is a very potent inhibitor of PDGF receptor autophosphorylation in intact cells which indicates that this compound will be active in vivo and that therapeutic concentrations should be readily achievable.

To determine if 292 selectively inhibits the PDGF receptor tyrosine kinase, its effect on the closely related EGF and FGF receptor tyrosine kinases was evaluated. Surprisingly, no detectable inhibition of EGF or FGF receptor autophosphorylation was observed at concentrations of 292 as high as 30 uM whereas the EGF receptor was inhibited by K252a (IC50=1 mM) (Table 2).

The src PTK family is related to the receptor PTKs because these proteins share 60–80% amino acid sequence identity in their enzymatic tyrosine kinase domains and also mediate intracellular signaling leading to cellular proliferation. Unlike the receptor PTKS, the src proteins do not contain extracellular or transmembrane domains and therefore do not function directly as receptors for extracellular stimuli. To further test the specificity of 292, its ability to inhibit the activity of recombinant c-src (UBI catalog# 14–117) was evaluated. In order to adapt this assay to a 96-well microtiter plate format, 0.5 mg of src-substrate peptide-2 (UBI cat #12–140) was added to each well in 23 mM Tris at pH 8.0, 68 mM NaCl, 14 mM ammonium bicarbonate and 0.01% sodium azide. After peptide immobilization, the wells were washed and then blocked with 25 mM HEPES pH 7.6, 100 mM NaCl, 0.2% Tween 20. The kinase reaction was initiated by adding to each well 100 ml of reaction mixture of contained test compounds at 0.03–30 mM, 50 mM ATP and 10 units of c-src in 50 mM Tris; pH 7, 25 mM $MnCl_2$; 5 mM $MnCl_2$; 0.05 mM $Na_3VO_4$; 100 mM HEPES pH 7; 5% Glycerol and 0.05% nonylphenoxy polyethoxy ethanol (NP-40). After a 20 minute incubation at 37° C., the reactions were stopped by adding 10 ul of 50% acetic acid, the wells were washed and antiphosphotyrosine antibody was used to detect the tyrosine phosphorylated substrate under the same conditions as described above for the detection of phosphorylated PDGF receptor. Compound 292 inhibited src kinase with an $IC_{50}=$ 1.0 uM which was a 160-fold higher concentration than that required to inhibit PDGF receptor autophosphorylation. On the other hand, staurosporin and K252a blocked src kinase activity with $IC_{50}$ values of 70 nM and 20 nM, respectively. These results demonstrate that, whereas 292 is highly selective for inhibiting PDGF receptor kinase activity, staurosporin and K252a are equally or more potent at inhibiting src kinase activity.

In spite of the fact that staurosporin efficiently inhibits receptor tyrosine kinases, staurosporin was originally discovered because it potently inhibited protein kinase C activity. This demonstrates that protein kinase inhibitors can have a broad spectrum of activity against a variety of tyrosine kinases as well as the more distantly related serine/threonine kinases. To investigate the possibility that 292 may inhibit serine/threonine protein kinases, Protein Kinase A (PKA) and Protein Kinase C (PKC) assays were performed using UBI's non-radioactive kinase assay under the conditions described by the manufacturer (UBI, Cat # 17–112). Compound 292 was compared to staurosporin and K252a by testing each of these compounds over a concentration range of 0.025–40 uM. As shown in Table 2, compound 292 did not achieve a 50% reduction in either PKC or PKA activity at a concentration of 40 uM which is>6000-fold higher than the concentration required to inhibit PDGF receptor kinase activity. K252a was found to be the most potent inhibitor of these serine/threonine kinases with an IC50 of 70 nM for PKA and 100 nM for PKC while staurosporin inhibited both kinases with an $IC_{50}=70$–80 nM. These results demonstrate that while some kinase inhibitors such as staurosporin and K252a lack selectivity, 292 is>100 fold more selective for PDGF receptor than for other receptor tyrosine kinases, src kinases and serine/threonine kinases. Such selectivity greatly enhances the therapeutic potential of 292 for the treatment of diseases believed to be at least in part mediated by PDGF such as atherosclerosis, certain cancers, glomerulonephritis and restenosis following angioplasty.

TABLE 2

| | Inhibition of Protein Kinase Activity IC50 [μM] | | | | | |
|---|---|---|---|---|---|---|
| Compound | βPDGFR | EGFR | FGFR | src-kinase | PKA | PKC |
| 292 | 0.006 | >30 | >30 | 1.000 | >40 | >40 |
| K525a | 0.270 | 1.0 | ND[1] | 0.020 | 0.070 | 0.100 |
| Staurosporin | 0.070 | ND | ND | 0.070 | 0.070 | 0.080 |

[1]Not Determined

Inhibition of Cell Proliferation by 292

Figure 2:
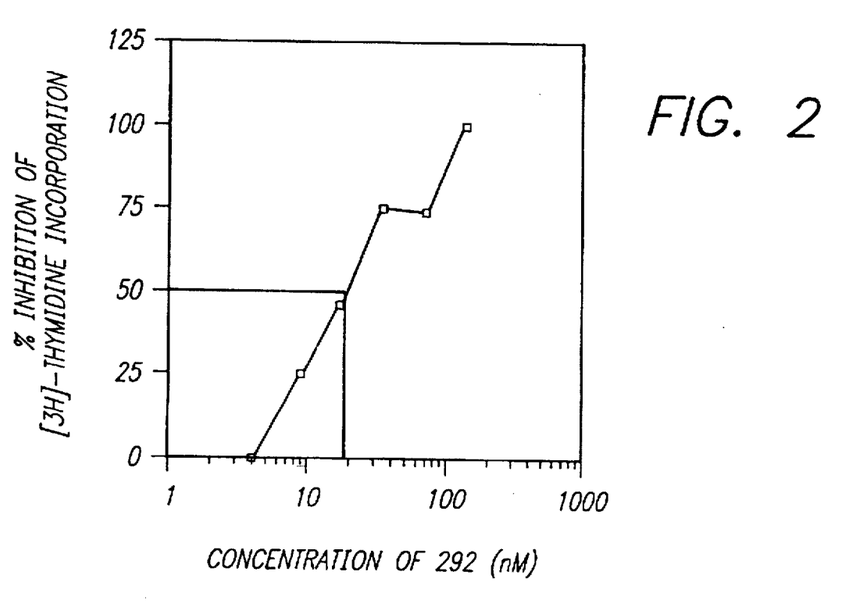
FIG. 2 shows the effect of compound 292 on PDGF BB-induced [$^3$H] thymidine incorporation into HS68 cells.

In order to determine the potential therapeutic utility of a PTK inhibitor it is important to demonstrate the inhibitor's ability to block cellular proliferation in response to a growth factor that is involved in mediating a proliferative disorder. Since there are many reports in the literature implicating PDGF in diseases such as glomerulonephritis, cancer, atherosclerosis, and restenosis we tested 292 for its ability to block PDGF induced cell proliferation. A human primary fibroblast cell line, HS68 (ATCC), was plated into 96 well dishes at 150,000 cells/well in media containing 10% fetal bovine serum in DMEM. The cells were incubated at 37° C. for 7–10 days at which time they had become confluent and quiescent. Compound 292 was added in a concentration range of 5–120 nM; 30 minutes later the cells were stimulated by the addition of 50 ng/ml of PDGF BB and incubation was continued at 37° C. for 18 hours. To determine the level of cell proliferation, 2 mCi of [$^3$H] thymidine were added to each well and incubation was continued for an additional 5 hours. Cells were then washed with 5% cold trichloroacetic acid (TCA), solubilized in 0.2N NaOH, 0.1% SDS and the amount of [³H] thymidine incorporation was determined. Routinely a 5-10 fold increase in thymidine incorporation was observed in cells treated with PDGF BB as compared to untreated cells (data not shown). As shown in FIG. 2, compound 292 blocked PDGF BB induced thymidine incorporation by 50% at 16 nM and completely inhibited mitogenicity at 120 nM. These concentrations of 292 correlate very closely with those required to block PDGF receptor phosphorylation in HR5 cells.

To determine if 292 exerts a nonspecific antiproliferative effect or is cytotoxic, its effects on the proliferation of human cell lines (e.g. HS68, HS 27, CCD18, and WS1 obtained from ATCC) was determined under standard tissue culture conditions. Cells were sparsely seeded in standard tissue culture medium containing 10% fetal bovine serum at 3.5× $10^3$ cells /well in a 96-well microtiter plate (Falcon) in the absence or presence of 292, staurosporin or K252a in the concentration range of 0.01-30 uM. The cells were then allowed to grow under standard tissue culture conditions for 96 hours, at which time they were fixed with 3.3% glutaraldehyde, washed with $H_2O$ and stained with 0.05% methylene blue (Sigma). Following staining, the cells were washed, the dye was eluted with 3% HCl and absorbance was monitored at 665 nM using a plate reader (Molecular Devices). The percentage of inhibition of cell proliferation was determined by comparing the absorbance observed in the presence of compound with the absorbance obtained in the absence of inhibitor. As shown in Table 3, no decrease in cell growth of any of the cell lines tested was observed following treatment with 292 at concentrations up to 10 uM and only a slight decrease (10-20%) occurred at 30 uM. In contrast, staurosporin completely blocked the growth of all of the cell lines at 10 nM and K252a inhibited cell growth by 50% in the concentration range of 1-12 uM with CCD 18 cells being the most sensitive. These results demonstrate that stautosporin, which is a nonspecific protein kinase inhibitor, also exerts a nonspecific antiprolifertive or cytotoxic effect at the same concentrations required to inhibit kinase activity. On the other hand, 292 had no effect on the growth of HS68 cells under standard tissue culture conditions at a concentration 1000-fold higher than those required to block PDGF induced mitogenesis of these cells. These results indicate that the inhibition of PDGF receptor kinase activity to achieve a therapeutic effect should be occur at 292 concentrations far below those that cause cytotoxic effects.

TABLE 3

Inhibition of Cell Proliferation Under Normal Tissue Culture Condition $IC_{50}$ [μM]

| ASSAY | CCD18 | HS27 | WS1 | HS68 |
| --- | --- | --- | --- | --- |
| Inhibitor 292 | >30 | >30 | >30 | >30 |
| Staurosporin | <0.01 | <0.01 | <0.01 | <0.01 |
| K252a | 1 | 12 | 5 | 5 |

All publications and patent applications cited herein are incorporated by reference to the same extent as if each individual publication or application was specifically and individually indicated to be incorporated by reference.

It should be understood that the invention is not limited to the particular embodiments shown and described herein, but that various changes and modifications may be made without departing from the spirit and scope of this novel concept as defined by the following claims.

We claim:

1. A method for inhibiting a protein kinase, which comprises:

contacting a composition containing a protein kinase with a compound of the formula wherein:

$R_1$ is H, lower alkyl, or lower alkanoyl;

$R_2$ is H, lower alkyl, or lower alkanoyl;

$R_3$ and $R_4$ together represent a cis double bond, $R_5$ is =O;

$R_6$ and $R_7$ together represent a double bond or —O— or each of $R_6$ and $R_7$ independently represents H or OR;

$R_8$ and $R_9$ together represent a double bond or —O— or each of $R_8$ and $R_9$ independently represents H or OR, and each R independently represents H, lower alkyl, or lower alkanoyl, in an amount effective to inhibit said protein kinase.

2. The method of claim 1, wherein $R_1$ represents lower alkyl.

3. The method of claim 1, wherein $R_2$ represents H.

4. The method of claim 1, wherein $R_6$ and $R_7$ each represents OH.

5. The method of claim 1, wherein $R_8$ and $R_9$ represent a double bond or —O—.

6. The method of claim 1, wherein $R_1$ represents $CH_3$, $R_2$ represents H $R_6$ and $R_7$ each represents OH, and $R_8$ and $R_9$ represent a double bond or —O—.

7. The method of claim 1, wherein the carbon at position 8 has an S configuration and the carbon at position 9 has an S configuration.

8. The method of claim 1, wherein the carbon at position 3 has an S configuration.

9. The method of claim 1, wherein said contacting occurs in vivo.

10. The method of claim 1, wherein said composition comprises a body fluid of a mammal.

11. The method of claim 11, wherein said body fluid is blood or a blood fraction.

12. The method of claim 10, wherein said kinase is a tyrosine kinase.

13. The method of claim 10, wherein said tyrosine kinase is PDGF.

14. The method of claim 10, wherein said method further comprises measuring tyrosine kinase activity in said body fluid in the presence and absence of said compound and relating said kinase activity to concentration of tyrosine kinase or a substrate for tyrosine kinase in said composition.

15. A pharmaceutical composition for the treatment of a kinase dependent disease in a mammal, comprising a compound of the formula wherein:

$R_1$ is A. lower alkyl, or lower alkanoyl;

$R_2$ is H, lower alkyl, or lower alkanoyl;

$R_3$ and $R_4$ together represent a cis double bond;

$R_5$ is =;

$R_6$ and $R_7$ together represent a double bond or —O— or each of $R_6$ and $R_7$ independently represents H or OR;

$R_8$ and $R_9$ together represent a double bond or —O— or each of $R_8$ and $R_9$ independently represents H or OR; and each R independently represents H, lower alkyl, or lower alkanoyl;

in an amount effective to inhibit tyrosine kinase in a pharmaceutically acceptable carrier.

16. The composition of claim 15, wherein $R_1$ represents $CH_3$, $R_2$ represents H, $R_6$ and $R_7$ each represents OH, and $R_8$ and $R_9$ represent a double bond or —O—.

17. The composition of claim 15, wherein $R_1$ represents $CH_3$, $R_2$ represents H, $R_6$ and $R_7$ represent a double bond or —O—, and $R_8$ and $R_9$ represent a double bond or —O—.

18. The composition of claim 17, wherein the carbon at position 8 has an S configuration and the carbon at position 9 has an S configuration.

19. The composition of claim 17, wherein the carbon at position 3 has an S configuration.

20. A method of controlling a kinase dependent disease which comprises administering to a mammal suffering from a kinase dependent disease a therapeutically effective amount of a compound of claim 1.

21. The method of claim 1, wherein:

$R_1$ is lower alkyl;

$R_2$ is H;

$R_6$ and $R_7$ together represent a double bond or —O— or each of $R_6$ and $R_7$ independently represents H or OR;

$R_8$ and $R_9$ together present a double bond or —O—; and each R independently represents H, lower alkyl, or lower alkanoyl.

22. The method of claim 20, wherein $R_1$ is lower alkyl.

23. The method of claim 20, wherein $R_2$ is H.

24. The method of claim 20, wherein $R_6$ and $R_7$ each represents OH.

25. The method of claim 20, wherein $R_8$ and $R_9$ represent a double bond or —O—.

26. The method of claim 20, wherein $R_6$ and $R_7$ represent —O—.

27. The method of claim 20, wherein $R_6$ and $R_7$ represent a double bond.

28. The method of claim 20, wherein $R_1$ represents $CH_3$, $R_2$ represents H, $R_6$ and $R_7$ each represents OH, and $R_8$ and $R_9$ represent a double bond or —O—.

* * * * *